(12) United States Patent
Buffkin, Jr. et al.

(10) Patent No.: US 11,406,324 B2
(45) Date of Patent: Aug. 9, 2022

(54) METHOD AND SYSTEM FOR MEASURING FLUID STATUS

(71) Applicant: Spectroflow, Inc., Portola Valley, CA (US)

(72) Inventors: Dan Eric Buffkin, Jr., Newberry, FL (US); Michael Dillhyon, Miami, FL (US); Stephen Zadig, Portola Valley, CA (US); Eric L. Olson, Barnstpale (GB)

(73) Assignee: Spectroflow, Inc., Portola Valley, CA (US)

( * ) Notice: Subject to any disclaimer, the term of this patent is extended or adjusted under 35 U.S.C. 154(b) by 0 days.

(21) Appl. No.: 17/146,826

(22) Filed: Jan. 12, 2021

(65) Prior Publication Data

US 2021/0128063 A1    May 6, 2021

Related U.S. Application Data

(63) Continuation-in-part of application No. 16/685,486, filed on Nov. 15, 2019, now Pat. No. 10,921,244.
(Continued)

(51) Int. Cl.
*A61B 5/02* (2006.01)
*A61B 5/00* (2006.01)
(Continued)

(52) U.S. Cl.
CPC ........ *A61B 5/6804* (2013.01); *A61B 5/02422* (2013.01); *A61B 5/02433* (2013.01);
(Continued)

(58) Field of Classification Search
CPC ..... A61B 5/0205; A61B 5/002; A61B 5/0022; A61B 5/02007; A61B 5/02042;
(Continued)

(56) References Cited

U.S. PATENT DOCUMENTS 7,613,504 B2   11/2009   Rowe
8,644,911 B1   2/2014   Panasyuk et al.
(Continued)

FOREIGN PATENT DOCUMENTS

WO   WO-2011114025 A2 *   9/2011   ............. A61F 13/08
WO   WO-2017120387 A1 *   7/2017   ........ H04M 1/72412
WO   WO-2017215409 A1 *   12/2017   ........... A61B 5/0002

OTHER PUBLICATIONS

International Search Report in corresponding International Application No. PCT/US2019/061753, dated Mar. 5, 2020.

*Primary Examiner* — Michael P Stafira
(74) *Attorney, Agent, or Firm* — Young Basile Hanlon & MacFarlane, P.C.

(57) ABSTRACT

A compression garment may be used for measuring fluid buildup in a subcutaneous tissue space. The compression garment may include a processor, an emitter, and a detector. The emitter and the detector are coupled to the processor. The emitter may be configured to emit a signal into a subcutaneous tissue space of a subject. The signal may be reflected by the subcutaneous tissue space. The detector may be configured to receive the reflected signal. The processor may be configured to determine a fluid status in the subcutaneous tissue space. The fluid buildup in the subcutaneous tissue space may be based on an energy level of the reflected signal.

18 Claims, 4 Drawing Sheets

Related U.S. Application Data

(60) Provisional application No. 62/768,445, filed on Nov. 16, 2018.

(51) Int. Cl.
*A61B 5/024* (2006.01)
*A61B 5/1455* (2006.01)
*A61F 13/08* (2006.01)
*A61B 5/11* (2006.01)

(52) U.S. Cl.
CPC ...... *A61B 5/02438* (2013.01); *A61B 5/14552* (2013.01); *A61B 5/4878* (2013.01); *A61B 5/721* (2013.01); *A61B 5/7282* (2013.01); *A61B 5/742* (2013.01); *A61B 5/1118* (2013.01); *A61B 2562/0219* (2013.01); *A61B 2562/0238* (2013.01); *A61F 13/08* (2013.01)

(58) Field of Classification Search
CPC ..... A61B 5/021; A61B 5/02141; A61B 5/022; A61B 5/024; A61B 5/0295; A61B 5/418; A61B 5/4238; A61B 5/4255; A61B 5/4836; A61B 5/4842; A61B 5/4848; A61B 5/6812; A61B 5/6824; A61B 5/6828; A61B 5/6829; A61B 17/1325; A61B 5/1118; A61B 5/6804; A61B 5/01; A61B 2562/0219; A61B 2562/0238; A61B 5/0024; A61B 5/0082; A61B 5/02422; A61B 5/02433; A61B 5/02438; A61B 5/14551; A61B 5/14552; A61B 5/4878; A61B 5/721; A61B 5/7282; A61B 5/742; A61B 5/0537; A61B 5/14532; A61B 5/681; A61B 5/02055; A61B 5/1117; A61B 5/369; A61B 8/06; A61B 8/0808; A61B 8/565; A61B 5/0006; A61B 5/053; A61B 5/389; A61B 5/318; A61B 5/0008; A61B 5/1116; A61B 5/1112; A61B 5/026; A61B 7/00; A61B 5/6826; A61B 8/00; A61B 5/14546; A61B 2560/0223; A61B 5/0031; A61B 5/6803; A61B 5/14503; A61B 5/7264; A61B 5/4839; A61B 8/488; A61B 5/0077; A61B 5/145; A61B 5/6866; A61B 7/04; A61B 5/0013; A61B 5/0261; A61B 5/6806; A61B 5/6807; A61B 5/6891; A61B 7/045; A61B 5/7267; A61B 5/14539; A61B 5/411; A61B 8/56; A61B 5/726; A61B 5/4023; A61B 5/4806; A61B 5/7225; A61B 5/7275; A61B 5/14535; A61B 5/4519; A61B 5/4528; A61B 5/6816; A61B 10/007; A61B 8/4472; A61B 2018/00577; A61B 2018/00791; A61B 5/11; A61B 5/1451; A61B 5/208; A61B 5/4866; A61B 5/7203; A61B 5/15003; A61B 5/150755; A61B 5/150992; A61B 5/153; A61B 5/7278; A61B 2505/7257; A61B 5/746; A61B 2560/0214; A61B 5/0215; A61B 5/412; A61B 5/7214; A61B 5/02028; A61B 5/1459; A61B 5/398; A61B 5/7455; A61B 5/0816; A61B 5/14507; A61B 5/1495; A61B 5/150221; A61B 8/5223; A61B 18/1492; A61B 2017/00973; A61B 2018/0022; A61B 2090/378; A61B 5/02108; A61B 5/1114; A61B 5/1455; A61B 5/7465; A61B 17/11; A61B 18/02; A61B 2017/1103; A61B 2017/1107; A61B 2017/1139; A61B 2018/00642; A61B 2018/00797; A61B 5/0225; A61B 5/029; A61B 5/076; A61B 5/165; A61B 5/7405; A61B 50/10; A61B 50/13; A61B 2018/00434; A61B 2018/00744; A61B 2018/00875; A61B 2560/0219; A61B 2560/0468; A61B 5/1038; A61B 5/1113; A61B 5/112; A61B 5/1124; A61B 5/1128; A61B 5/113; A61B 5/1176; A61B 5/201; A61B 5/224; A61B 5/30; A61B 5/4076; A61B 5/4803; A61B 5/486; A61B 5/6822; A61B 5/6838; A61B 5/6898; A61B 5/7271; A61B 2018/00404; A61B 2018/00863; A61B 2034/252; A61B 2562/0214; A61B 5/0235; A61B 5/02416; A61B 5/1473; A61B 5/150213; A61B 5/150229; A61B 5/150358; A61B 5/150862; A61B 5/155; A61B 5/157; A61B 5/282; A61B 5/291; A61B 5/332; A61B 5/4833; A61B 5/6851; A61B 5/72; A61B 5/747; A61B 8/52; A61B 1/00154; A61B 1/313; A61B 17/02; A61B 17/0218; A61B 17/0293; A61B 2017/00867; A61B 2017/0243; A61B 2017/1135; A61B 2018/00666; A61B 2034/107; A61B 2090/306; A61B 5/05; A61B 5/14542; A61B 8/0891; A61B 8/4281; A61B 90/37; A61B 17/3417; A61B 2017/00088; A61B 2017/00092; A61B 2018/00005; A61B 2018/00023; A61B 2018/00273; A61B 2018/00386; A61B 2018/00494; A61B 2018/00511; A61B 2018/00517; A61B 2018/00648; A61B 2018/00672; A61B 2018/00815; A61B 2018/00839; A61B 2018/20361; A61B 2018/205547; A61B 2034/254; A61B 2090/065; A61B 2562/0257; A61B 34/35; A61B 5/0002; A61B 5/027; A61B 5/0285; A61B 5/1075; A61B 5/1126; A61B 5/14517; A61B 5/14556; A61B 5/150099; A61B 5/150267; A61B 5/150312; A61B 5/150389; A61B 5/150503; A61B 5/150572; A61B 5/150732; A61B 5/15074; A61B 5/150946; A61B 5/154; A61B 5/20; A61B 5/6892; A61B 6/037; A61B 8/42; A61B 90/30; A61B 90/70; A61B 2017/00221; A61B 2018/00285; A61B 2018/00714; A61B 2034/105; A61B 2090/064; A61B 2503/08; A61B 2560/0475; A61B 34/20; A61B 5/02; A61B 5/02152; A61B 5/03; A61B 5/0535; A61B 5/1135; A61B 5/349; A61B 5/4818; A61B 5/4872; A61B 5/4881; A61B 5/489; A61B 5/6823; A61B 5/6832; A61B 5/6852; A61B 5/6885; A61B 5/7217; A61B 5/7232; A61B 5/7235; A61B 6/032; A61B 7/003; A61B 8/0858; A61B 8/461; A61B 8/464; A61B 8/465; A61B 8/467; A61B 90/98; A61B 10/0048; A61B 10/0051; A61B 18/18; A61B 18/20; A61B 2010/0077; A61B 2018/00011; A61B 2034/101; A61B 5/0035; A61B 5/02255; A61B 5/14865; A61B 5/150259; A61B 5/163; A61B 5/352; A61B 5/4088; A61B 5/4869; A61B 5/6802; A61B 5/6813; A61B 5/749; A61B
8/04; A61B 8/065; A61B 8/0833; A61B
8/0841; A61B 8/0883; A61B 8/12; A61B
8/4218; A61B 8/466; A61B 8/483; A61B
8/485; A61B 1/00078; A61B 1/0052;
A61B 1/0055; A61B 1/12; A61B 17/00;
A61B 17/32; A61B 18/14; A61B
2017/00809; A61B 2018/00029; A61B
2018/00166; A61B 2018/1892; A61B
2034/2051; A61B 2034/2072; A61B
2090/373; A61B 2090/376; A61B
2090/3762; A61B 2560/0456; A61B
2562/162; A61B 3/16; A61B 5/0071;
A61B 5/028; G01N 15/1459; G01N
15/1404; G01N 15/1468; G01N 15/147;
G01N 2015/0065; G01N 2015/1006;
G01N 2015/149; G01N 33/48; G01N
2015/1406; G01N 2015/1415; G01N
2021/6439; G01N 21/63; G01N 21/6428;
G01N 33/5005; G01N 9/002; G01N
11/16; G01N 21/53; G01N 15/1436;
G01N 2009/006; G01N 15/1429; G01N
29/036; G01N 15/1434; G01N 15/1463;
G01N 15/1475; G01N 2015/1037; G01N
2015/1411; G01N 2015/1413; G01N
2015/1452; G01N 2015/1486; G01N
2021/058; G01N 33/18; G01N 33/49;
G01N 33/4915; G01N 33/5091; G01N
15/06; G01N 33/5094; G01N 1/30; G01N
2015/144; G01N 2015/1481; G01N
2291/02818; G01N 33/80; G01N
33/0004; G01N 11/04; G01N 25/00;
G01N 29/022; G01N 33/4905; G01N
21/49; G01N 2291/014; G01N 27/06;
G01N 33/5088; G01N 1/14; G01N
2015/1493; G01N 2800/2821; G01N
33/24; G01N 33/66; G01N 33/6896;
G01N 33/86; G01N 35/1097; G01N
11/02; G01N 2009/004; G01N 21/05;
G01N 2291/024; G01N 2291/0256; G01N
29/222; G01N 3/12; G01N 33/2823;
G01N 11/08; G01N 11/10; G01N 11/12;
G01N 2001/1418; G01N 2011/0086;
G01N 2035/00881; G01N 2035/0441;
G01N 2203/0019; G01N 3/02; G01N
33/1826; G01N 33/1833; G01N 33/1846;
G01N 33/1893; G01N 33/493; G01N
35/00871; G01N 35/1016; G01N
15/0826; G01N 2035/00237; G01N
21/4133; G01N 2203/0044; G01N
2291/02809; G01N 2291/02836; G01N
29/30; G01N 3/08; G01N 33/28; G01N
33/2847; G01N 33/5023; G01N 33/68;
G01N 5/02; G01N 5/025; G01N 7/14;
G01N 11/00; G01N 11/105; G01N
11/162; G01N 2011/0026; G01N
2021/1723; G01N 2035/1025; G01N
21/1717; G01N 21/3151; G01N 21/35;
G01N 21/645; G01N 21/65; G01N 21/85;
G01N 2291/0426; G01N 2291/0427;
G01N 2333/205; G01N 2333/96472;
G01N 27/74; G01N 29/343; G01N 3/00;
G01N 3/56; G01N 3/567; G01N 30/28;
G01N 30/90; G01N 33/146; G01N 33/15;
G01N 33/56922; G01N 33/573; G01N
33/582; G01N 35/025; G01N 9/24; G01N
1/24; G01N 1/38; G01N 1/4077; G01N
13/04; G01N 15/0656; G01N 19/08;
G01N 2011/0033; G01N 2015/0053;
G01N 2015/0073; G01N 2015/008; G01N
2015/0084; G01N 2015/084; G01N
2015/1409; G01N 2021/0346; G01N
2021/154; G01N 2021/3129; G01N
2021/3133; G01N 2021/3148; G01N
2021/317; G01N 2021/3595; G01N
2030/027; G01N 2035/1013; G01N
2035/1034; G01N 21/15; G01N 21/31;
G01N 21/3504; G01N 21/43; G01N
21/9027; G01N 2201/06153; G01N
2201/0627; G01N 2201/0638; G01N
2201/12; G01N 2223/634; G01N
2291/012; G01N 2291/0226; G01N
2291/0253; G01N 2291/0254; G01N
2291/0422; G01N 2291/101; G01N
2333/755; G01N 24/081; G01N 2474/20;
G01N 25/18; G01N 27/18; G01N 27/302;
G01N 27/4167; G01N 27/44704; G01N
29/024; G01N 29/0681; G01N 29/223;
G01N 29/228; G01N 29/348; G01N
29/46; G01N 3/068; G01N 30/02; G01N
30/74; G01N 33/0009; G01N 33/0027;
G01N 33/0047; G01N 33/2858; G01N
33/48785; G01N 35/1011; G01N 7/10;
G01N 9/00; G01N 1/00; G01N 1/2202;
G01N 1/2273; G01N 1/2813; G01N
1/286; G01N 11/14; G01N 13/00; G01N
13/02; G01N 15/0272; G01N 15/08;
G01N 15/082; G01N 15/1031; G01N
15/1056; G01N 15/1427; G01N 15/1484;
G01N 17/002; G01N 17/006; G01N
2001/002; G01N 2001/2223; G01N
2001/2279; G01N 2001/2285; G01N
2001/383; G01N 2011/147; G01N
2013/003; G01N 2013/0208; G01N
2013/0283; G01N 2015/0038; G01N
2015/0046; G01N 2015/0662; G01N
2021/0342; G01N 2035/00435; G01N
2035/00455; G01N 2035/1018; G01N
21/00; G01N 21/272; G01N 21/3577;
G01N 21/359; G01N 21/412; G01N
21/474; G01N 2201/0221; G01N
2201/062; G01N 2203/0075; G01N
2203/0256; G01N 2203/0676; G01N
2203/0682; G01N 2291/02466; G01N
2291/02475; G01N 2291/02827; G01N
2291/044; G01N 2333/195; G01N
2405/00; G01N 2405/04; G01N 2405/08;
G01N 2570/00; G01N 27/185; G01N
27/226; G01N 27/4067; G01N 27/447;
G01N 27/622; G01N 27/624; G01N
2800/224; G01N 2800/26; G01N 29/11;
G01N 3/06; G01N 30/724; G01N 31/10;
G01N 33/1866; G01N 33/222; G01N
33/2829; G01N 33/2888; G01N 33/487;
G01N 33/48735; G01N 33/4925; G01N
33/497; G01N 33/50; G01N 33/6803;
G01N 33/6848; G01N 33/6851; G01N
33/92; G01N 35/026; G01N 9/34; G01N See application file for complete search history.

(56) References Cited

U.S. PATENT DOCUMENTS

| | | |
|---|---|---|
| 9,271,676 B2 | 3/2016 | Alanen et al. |
| 2009/0326346 A1 | 12/2009 | Kracker et al. |
| 2013/0317367 A1 | 11/2013 | Shuler |
| 2016/0058133 A1* | 3/2016 | Fournier ................ A61B 5/091 63/3.1 |
| 2016/0140834 A1 | 5/2016 | Tran |
| 2016/0183813 A1* | 6/2016 | Naima ................ A61B 5/0537 600/479 |
| 2016/0249698 A1* | 9/2016 | Berzowska ........ A41D 13/1281 2/69 |
| 2016/0331314 A1 | 11/2016 | Bhansali et al. |
| 2017/0049336 A1 | 2/2017 | Hatch |
| 2017/0303830 A1 | 10/2017 | Klein et al. |
| 2018/0021199 A1* | 1/2018 | Halbrecht .............. A61H 1/008 601/27 |

\* cited by examiner

METHOD AND SYSTEM FOR MEASURING FLUID STATUS

CROSS-REFERENCE TO RELATED APPLICATION

This application is a continuation-in-part of U.S. application patent Ser. No. 16/685,486, filed Nov. 15, 2019, which claims priority to and the benefit of U.S. Provisional Application Patent Ser. No. 62/768,445, filed Nov. 16, 2018, the entire disclosure of which is hereby incorporated by reference.

TECHNICAL FIELD

This disclosure relates to a medical device.

BACKGROUND

Edema may be caused by a variety of disease states. Treatment of edema often requires periodic or continuous monitoring. Current monitoring systems are inconvenient for the patient, expensive, and fail to provide quantifiable and actionable data.

SUMMARY

Disclosed herein are implementations of methods and systems for measuring fluid buildup. Implementations may include a sensor assembly that is integrated into a watch band, discrete device band and/or band and module, hand held device, or a module attached to a phone case. In some implementations, the sensor assembly may be integrated into a diagnostic tool. Additionally, the sensor assembly may be integrated into therapeutic items such as wearable compression garments, pneumatic compression devices, casts, bandages, or other such medical dressings.

In an aspect, a compression garment may be constructed of a compression fabric. The compression garment may include a processor and one or more sensors. The one or more sensors may each include an emitter, and a detector. The emitter and the detector are coupled to the processor. The emitter may be configured to emit a signal into a subcutaneous tissue space of a subject. The signal may be reflected by the subcutaneous tissue space. The detector may be configured to receive the reflected signal. The processor may be configured to determine a fluid buildup in the subcutaneous tissue space. The fluid buildup in the subcutaneous tissue space may be based on an energy level of the reflected signal.

In another aspect, a compression garment may be constructed of a compression fabric. The compression garment may include a sensor. The sensor may include a processor, an emitter, and a detector. The emitter and the detector are coupled to the processor. The emitter may be configured to emit a signal into a subcutaneous tissue space of a subject. The signal may be reflected by the subcutaneous tissue space. The detector may be configured to receive the reflected signal. The processor may be configured to determine a fluid buildup in the subcutaneous tissue space. The fluid buildup in the subcutaneous tissue space may be based on an energy level of the reflected signal.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
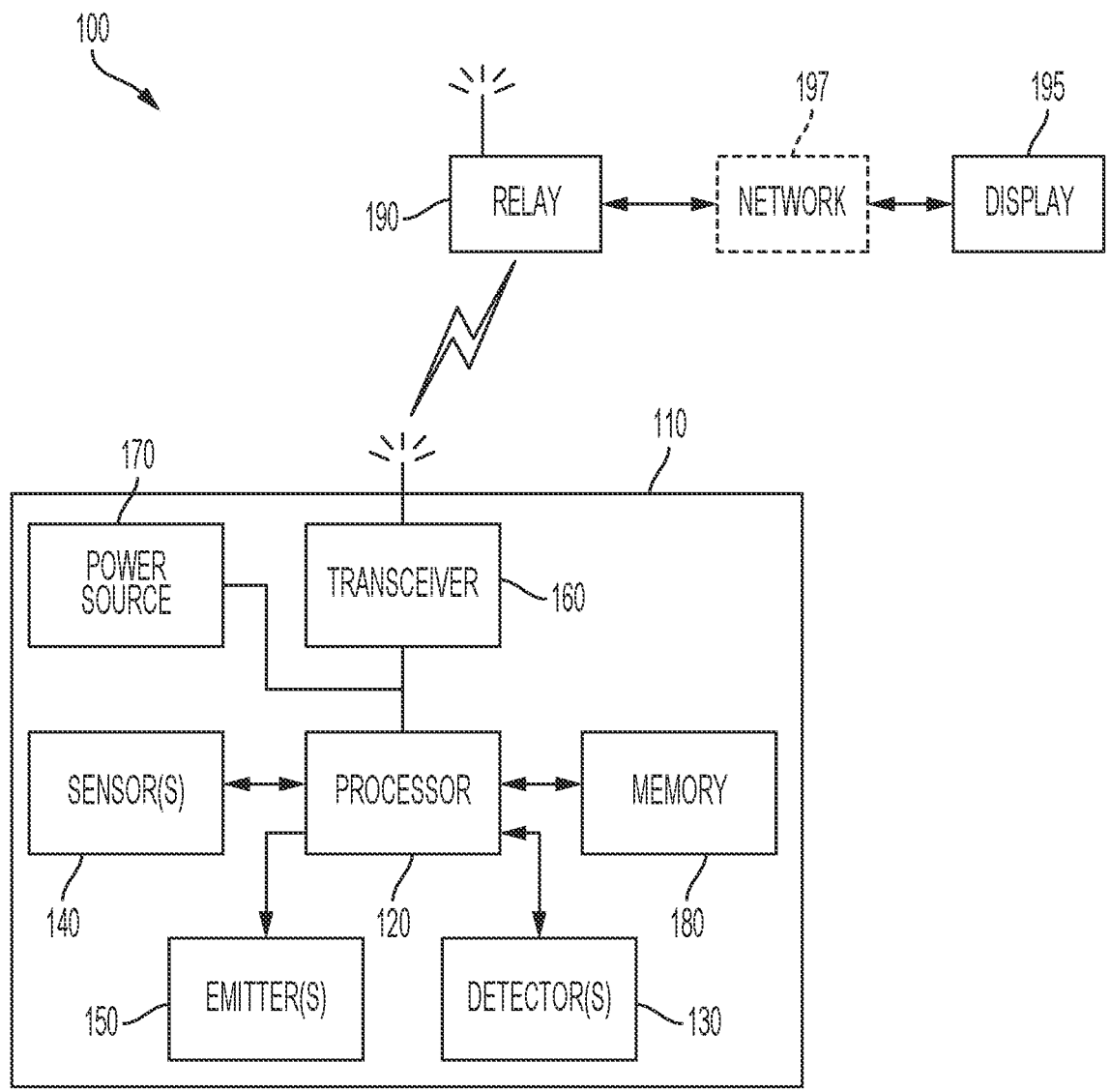
FIG. 1 is a block diagram of an example of a subcutaneous fluid detection system in accordance with embodiments of this disclosure.

FIG. 1 is a diagram of an example of a subcutaneous fluid detection system 100. The subcutaneous fluid detection system 100 may be used to detect fluid in a subcutaneous region of a subject. The subcutaneous fluid detection system 100 may be configured to quantify the detected fluid to determine a disease state of the subject. For example, the subcutaneous fluid detection system may be used to detect and manage fluid buildup associated disease states such as congestive heart failure (CHF), chronic obstructive pulmonary disease (COPD), chronic kidney disease (CKD), lymphedema, and venous insufficiency edema.

The subcutaneous fluid detection system 100 may include a device 110. The device 110 may be a wearable device or a diagnostic tool. The device 110 may be configured to be worn on a wrist, arm, leg, or any other suitable body part of a subject. The device 110 may be a watch, a bracelet, an armband, a finger ring, a headband, a wand, a probe, a compression garment, a pneumatic compression device, a casts, a bandage, or any other suitable device or medical dressing. The device 110 includes a processor 120, one or more detectors 130, one or more sensors 140, one or more emitters 150, a transceiver 160, a power source 170, and a memory 180.

The processor 120 may include one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

The processor 120 may be programmed to send instructions to the one or more emitters 150 and receive signals from the one or more detectors 130. The instructions may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

The instructions may include algorithms that may be utilized to improve signal quality, detection and timing. The processor 120 may control the timing of events. Algorithms may be used to refine signal quality received from the sensor system. This may include information from a tri-axial accelerometer, a sensor (e.g., for melanin readings to make appropriate signal adjustments), time of day, or any other sensor information. Predictive algorithms may track the information gathered so that proactive measures may be taken to maintain the health of a subject and avert crisis. General algorithms may be applied to optimize system performance, data collection and use.

The algorithms may be used to calculate the signal assessments as to positive (vs false positive) buildup of fluid. For example, once data has been taken over a large unit of subjects, an algorithm may be used to compensate for motion artifacts that may cause signal distortion at the interface between the sensor and the body. Another example would be to anticipate the impact of exercise on fluid buildup such that muscle flexing (as in the case of walking) has a tendency to purge fluid or inversely, passive sitting (as on an airplane) would cause fluid to naturally build up. In this way, the tri-axial accelerometer may be a source of information to feed such algorithms. Heart rate, respiration, and other sensor data may be factored in to algorithms to detect sub clinical edema in peripheral edema, pulmonary edema, or both. The algorithms may be tuned to be patient specific.

The one or more emitters 150 may each be a single wavelength LED emitter. In some embodiments, the one or more emitters 150 may each be a broadband emitter. Each of the one or more emitters may emit a 960 nm to 980 nm wavelength signal onto the skin of a subject. In an embodiment, the one or more emitters may emit a 970 nm wavelength signal. Each signal has a wavelength energy, and may penetrate the tissue of a subject to a depth of approximately 3-10 mm, for example a subcutaneous region. The signals from the one or more emitters 150 penetrate into the subcutaneous region and are reflected towards the one or more detectors 130.

The one or more detectors 130 may be any type of detector that is configured to detect light. For example, the one or more detectors 130 may include near infrared (NIR) spectrometer detectors, ultraviolet (UV) light detectors, visible light detectors, infrared spectrum detectors such as photodetectors, phototransistors, or photodiodes, or any combination thereof. The one or more detectors 130 are configured to receive the reflected light signals from the one or more emitters 150. The one or more detectors 130 are configured to measure an energy level of the received signals. The processor 120 is configured to determine a relative fluid content of the tissue based on the energy level of the received signals. For example, should the fluid level increase, less energy will be reflected to the one or more detectors 130 and the signal will decrease. Conversely, if less fluid is present, the signal level will increase. In this manner, the subcutaneous fluid detection system may measure and monitor the fluid content of a subject, for example to determine sub-clinical peripheral edema.

In an example, a method may include measuring a baseline value using the one or more detectors 130. The method may include performing periodic measurements. The periodicity and duration of the measurements may be configurable. An interval may be defined as the time between two measurements. Each measurement may be stored and tracked over time. The method may include measuring a slope of the measurements at each interval. An indication of sub-clinical peripheral edema may be determined if the slope of an interval is determined to be above a threshold.

In some embodiments, additional LED wavelength emitters may be included to support reflective pulse oximetry measurements to provide information regarding oxygen saturation that may be correlated to respiration, lung performance, or both. This information may be used to determine whether the subject has, for example, pulmonary edema. Additionally, with this signal, pulse and respiration can be captured for analysis. These additional LED wavelength emitters may be configured to emit 640 nm wavelength signals, 660 nm wavelength signals, 940 nm wavelength signals, or any combination thereof. In some embodiments, additional LED wavelength emitters may be included to detect melanin content to determine skin pigmentation to support error correction for energy absorption due to skin pigmentation. In some embodiments, one or more radio frequency (RF) emitters may be included for use in the detection of fluid status in the subcutaneous tissue space (e.g., interstitial space). For example, a 100-1000 MHz RF emitter and corresponding detector may be used.

The one or more sensors 140 may be any type of sensor and not limited to an accelerometer, a global positioning system (GPS), a barometer, or a thermocouple. In some embodiments, a tri-axial accelerometer may be utilized to improve overall understanding the of the conditions under which measurements are taken. The accelerometer may be controlled by the processor 120. In an example, a tri-axial accelerometer may be configured to indicate the activity and posture of the subject to improve the assessment of the signal conditions and reduce motion artifacts that could impact signal quality. If the subject is active, sedentary or supine, pooling or movement of fluid may normally occur which could potentially create false positives or negatives. An activity value may be generated based on the sensor data to determine an activity status of the user to reduce false positives.

The transceiver 160 may communicate with a relay 190 via Bluetooth, Bluetooth Low Energy, WiFi, or any other wireless transmission technology. The relay 190 may be configured to receive analysis/results from the transceiver 160 of the wearable device 110 and display the analysis/results on a user interface 195. In some embodiments, the relay 190 may receive raw data from the transceiver 160 of the wearable device 110 and transmit the raw data to a network device 197. The network device 197 may be configured to determine a relative fluid content of the tissue based on the raw data associated with an energy level of the received signals. For example, should the fluid level increase, less energy will be reflected and the signal will decrease. Conversely, if less fluid is present, the signal level will increase. In this manner, the subcutaneous fluid detection system may measure and monitor the fluid content of a subject, for example to determine sub-clinical peripheral edema. The network device 197 may be configured to transmit the analysis/results to the user interface 195 for display or storage. The network device may be a cloud based system that is configured to receive, store, and process information to run predictive algorithms for review by caregivers (e.g., clinicians, etc.). The caregivers may send instructions to the wearable device 110 for further measurement information and alert the subject of actions that need to be taken. The user interface 195 may include a cell phone, tablet/PC or discrete hub device that is connected to the internet via cellular modem, WiFi, direct cable, or any other communication link.

The power source 170 may be an integrated rechargeable battery. Alternatively, the power source 170 may be a primary battery.

The memory 180 may include any computer-usable or computer-readable medium or device that can tangibly contain, store, communicate, or transport any signal or information that may be used by or in connection with any processor, for example processor 120. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof. Information derived from the one or more sensors 140, processor 120, one or more detectors 130, or any combination thereof, may be stored in the memory 180 until such time as it is available to be transmitted via the transceiver 160 to the relay 190.

Figure 2:
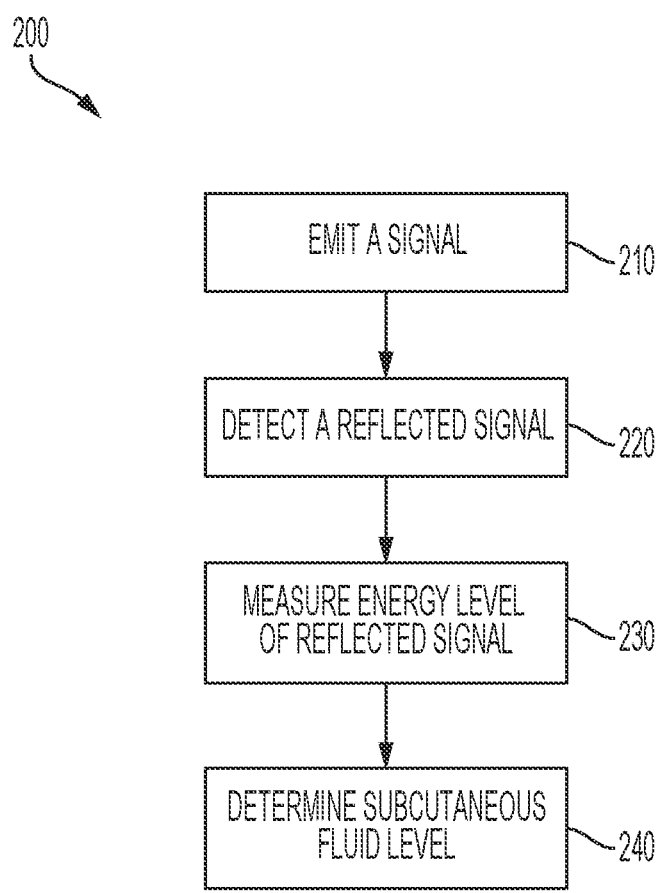
FIG. 2 is a flow diagram of an example method for detecting subcutaneous fluid.

FIG. 2 is a flow diagram of an example method 200 for detecting subcutaneous fluid. The method 200 include emitting a signal 210. The signal may be a light signal such as an LED light signal, or the signal may be an RF signal. Example LED light signals include, and are not limited to 970 nm±10 nm, 640 nm±10 nm, 660 nm±10 nm, or 940 nm±10 nm. For example, a 660 nm and 940 nm wavelengths may be used to detect peripheral capillary oxygen saturation (SPO2) and in some instances, heart and respiration rates. Pulse rate may be detected by cycling LED light signals such that they detect the passage of red blood cells as they move through the measurement area. Each LED light signal is emitted at a predetermined energy level. The LED light signals penetrate the skin into the subcutaneous tissue region where it is reflected back towards the skin of the subject. The method 200 includes detecting 220 the reflected signal. The method 200 includes measuring 230 an energy level of the reflected signal. The method 200 includes determining 240 a subcutaneous fluid level. The subcutaneous fluid level may be determined based on the energy level of the reflected signal.

Figure 3:
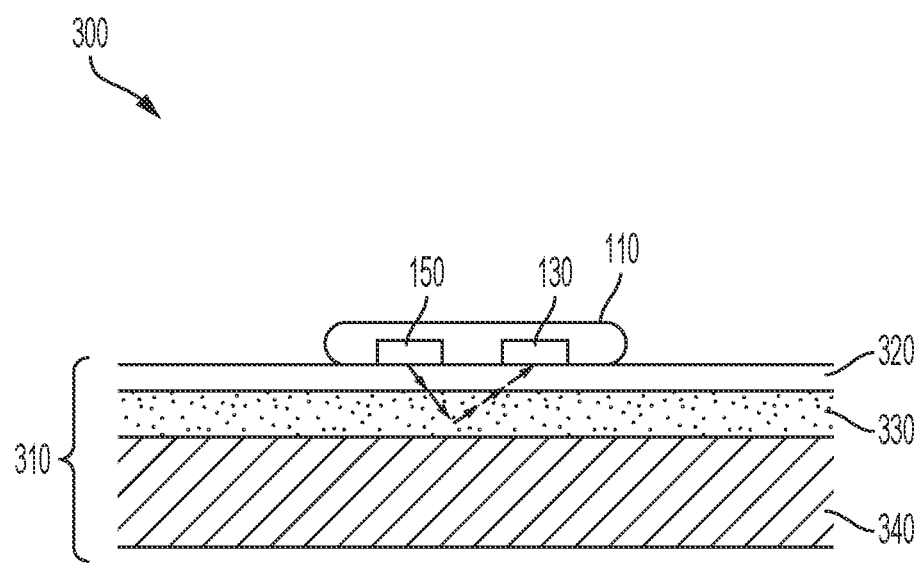
FIG. 3 is a diagram of a cross-sectional view of the subcutaneous fluid detection system of FIG. 1 on a subject in accordance with embodiments of this disclosure.

FIG. 3 is a diagram of a cross-sectional view of the device 110 of FIG. 1. Referring to FIG. 3, a cross-section of a portion of a subject body part 310 is shown. The body part may be an arm, a leg, a wrist, a finger, or any other suitable body part. As shown in FIG. 3, the body part 310 includes an epidermis (i.e., skin) layer 320, a subcutaneous tissue layer 330, and a muscle layer 340.

As shown in FIG. 3, a device 110 is placed on or in proximity to the epidermis layer 320. The emitter 150 is positioned at an angle to provide reflection of energy into the tissue to an optimal depth of 5 mm in the subcutaneous target region. The emitted energy, for example 970 nm wavelength NIR light, may be reflected to the detector 130, for example an NIR Solid State Digital Spectrometer/detector or silicon photodetector. The detector 130 may be positioned at an angle to receive the reflection of energy from the tissue. In some embodiments, other wavelengths may be used, for example any wavelength from 480-1030 nm. The transceiver may employ Bluetooth, Bluetooth Low Energy, WiFi or other transmission technologies as appropriate for best battery life and transmission conditions.

Figure 4:
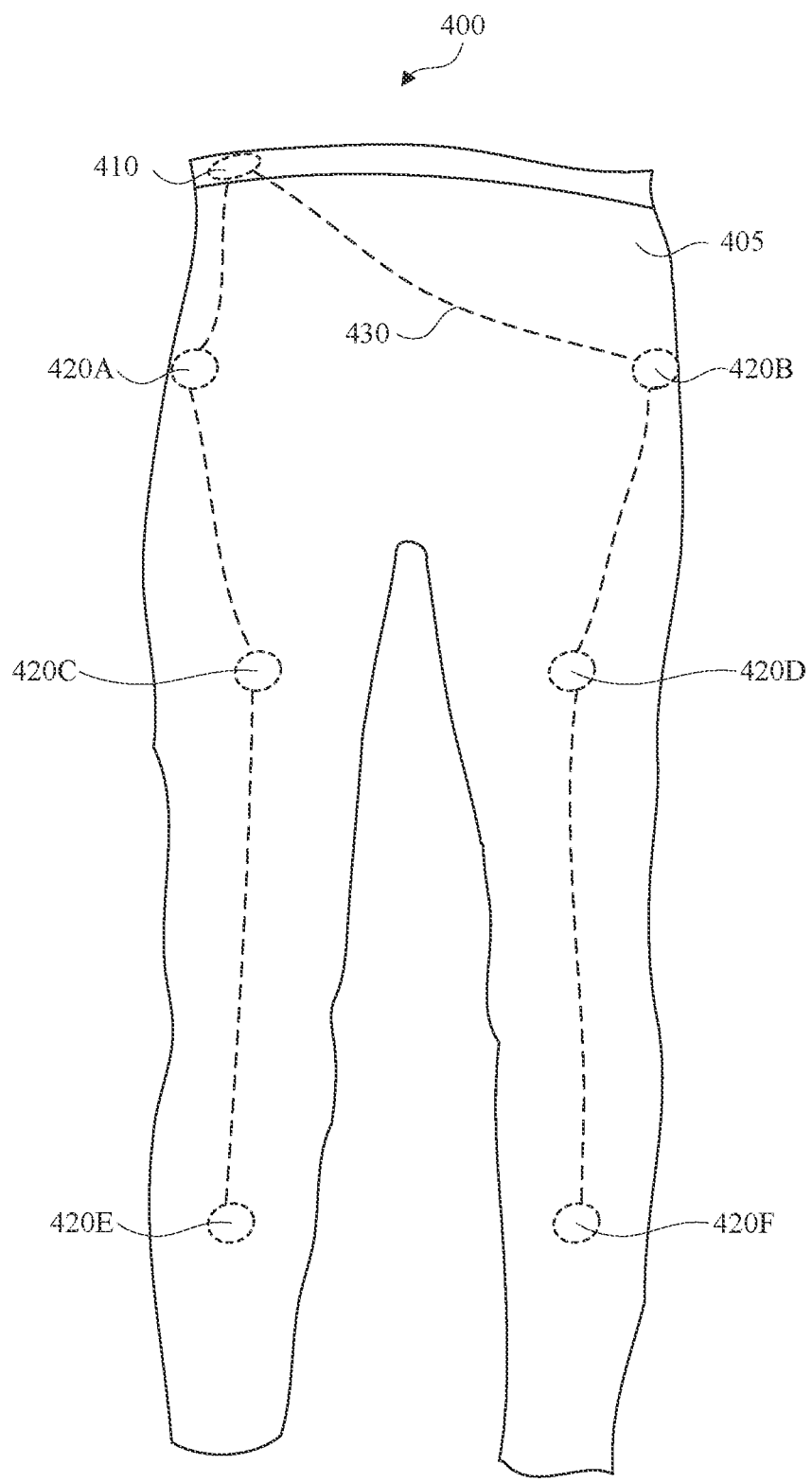
FIG. 4 is a diagram of an example of a compression garment for subcutaneous fluid detection in accordance with embodiments of this disclosure.

FIG. 4 is a diagram of an example of a compression garment 400 for subcutaneous fluid detection in accordance with embodiments of this disclosure. The compression garment 400 may be constructed of a fabric 405, such as an elastane fabric or similar elastic material, and in some examples may be in combination with nylon or polyester or denier 40, 60 or similar elastic material. The compression garment 400 may be configured to monitor and reduce fluid buildup in the underlying tissues and may have a compression value of approximately 5 mmHg to 50 mmHg. The compression garment 400 is shown as a pair of pants, however it is understood that the compression garment 400 may be implemented as any type of garment, for example a shirt, headband, sleeve, or the like. As shown in FIG. 4, the compression garment 400 includes a processing module 410 and one or more sensors 420A-420F. The one or more sensors 420A-420F may be electrically coupled to the processing module 410 via a communication link 430. The communication link 430 may be configured to send power to the one or more sensors 420A-420F. The communication link 430 may be configured to send and receive data to and from the one or more sensors 420A-420F.

The processing module 410 includes a processor, such as processor 120 shown in FIG. 1, a power source, such as power source 170 shown in FIG. 1, and a memory, such as memory 180 shown in FIG. 1. In some examples, the processing module 410 may include a transceiver, such as transceiver 160 shown in FIG. 1. The one or more sensors 420A-420F may each include one or more detectors such as detector 130 shown in FIG. 1, one or more sensors, such as sensor 140 shown in FIG. 1, one or more emitters, such as emitter 150 shown in FIG. 1, or any combination thereof.

The processor of the processing module 410 may include one or more processors, such as one or more special purpose processors, one or more digital signal processors, one or more microprocessors, one or more controllers, one or more microcontrollers, one or more application processors, one or more CPUs, one or more GPUs, one or more DSPs, one or more ASICs, one or more application specific standard products, one or more field programmable gate arrays, any other type or combination of integrated circuits, one or more state machines, or any combination thereof.

The processor of the processing module 410 may be programmed to send instructions to the one or more emitters of any of sensors 420A-420F via communication link 430 and receive signals from the one or more detectors of the sensor 420A-420F. The instructions may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

The instructions may include algorithms that may be utilized to improve signal quality, detection and timing. The processor of the processing module 410 may control the timing of events. Algorithms may be used to refine signal quality received from the sensor system. This may include information from a tri-axial accelerometer, a sensor (e.g., for melanin readings to make appropriate signal adjustments), time of day, or any other sensor information. Predictive algorithms may track the information gathered so that proactive measures may be taken to maintain the health of a subject and avert crisis. General algorithms may be applied to optimize system performance, data collection and use.

The algorithms may be used to calculate the signal assessments as to positive (vs false positive) buildup of fluid. For example, once data has been taken over a large unit of subjects, an algorithm may be used to compensate for motion artifacts that may cause signal distortion at the interface between the sensor and the body. Another example would be to anticipate the impact of exercise on fluid buildup such that muscle flexing (as in the case of walking) has a tendency to purge fluid or inversely, passive sitting (as on an airplane) would cause fluid to naturally build up. In this way, the tri-axial accelerometer may be a source of information to feed such algorithms. Heart rate, respiration, and other sensor data may be factored in to algorithms to detect sub clinical edema in peripheral edema, pulmonary edema, or both. The algorithms may be tuned to be patient specific.

The compression garment 400 is configured with an opening on an internal portion of the garment such that the emitters and detectors of each of the sensors 420A-420F is in contact with the skin of a patient or subject when worn. The one or more emitters of each of the sensors 420A-420F may each be a single wavelength LED emitter. In some embodiments, the one or more emitters may each be a broadband emitter. Each of the one or more emitters may emit a 960 nm to 980 nm wavelength signal onto the skin of a subject. In an embodiment, the one or more emitters may emit a 970 nm wavelength signal. Each signal has a wavelength energy, and may penetrate the tissue of a subject to a depth of approximately 3-10 mm, for example a subcutaneous region. The signals from the one or more emitters 150 penetrate into the subcutaneous region and are reflected towards the one or more detectors 130.

The one or more detectors of each of the sensors 420A-420F may be any type of detector that is configured to detect light. For example, the one or more detectors may include near infrared (NIR) spectrometer detectors, ultraviolet (UV) light detectors, visible light detectors, infrared spectrum detectors such as photodetectors, phototransistors, or photodiodes, or any combination thereof. The one or more detectors are configured to receive the reflected light signals from the one or more emitters. The one or more detectors are configured to measure an energy level of the received signals. The processor of the processing module 410 is configured to determine a relative fluid content of the tissue based on the energy level of the received signals. For example, should the fluid level increase, less energy will be reflected to the one or more detectors and the signal will decrease. Conversely, if less fluid is present, the signal level will increase. In this manner, the subcutaneous fluid detection system may measure and monitor the fluid content of a subject, for example to determine sub-clinical peripheral edema.

In an example, a method may include measuring a baseline value using the one or more detectors. The method may include performing periodic measurements. The periodicity and duration of the measurements may be configurable. An interval may be defined as the time between two measurements. Each measurement may be stored and tracked over time. The method may include measuring a slope of the measurements at each interval. An indication of sub-clinical peripheral edema may be determined if the slope of an interval is determined to be above a threshold.

In some embodiments, additional LED wavelength emitters may be included to support reflective pulse oximetry measurements to provide information regarding oxygen saturation that may be correlated to respiration, lung performance, or both. This information may be used to determine whether the subject has, for example, pulmonary edema. Additionally, with this signal, pulse and respiration can be captured for analysis. These additional LED wavelength emitters may be configured to emit 640 nm wavelength signals, 660 nm wavelength signals, 940 nm wavelength signals, or any combination thereof. In some embodiments, additional LED wavelength emitters may be included to detect melanin content to determine skin pigmentation to support error correction for energy absorption due to skin pigmentation. In some embodiments, one or more radio frequency (RF) emitters may be included for use in the detection of fluid status in the subcutaneous tissue space (e.g., interstitial space). For example, a 100-1000 MHz RF emitter and corresponding detector may be used.

The one or more sensors 420A-420F may be any type of sensor and may include an accelerometer, a global positioning system (GPS), a barometer, or a thermocouple. For example, sensor 420A may be an accelerometer, sensor 420B may be a GPS sensor, sensor 420C may be a barometer, and sensor 420D may be a thermocouple. In some embodiments, a tri-axial accelerometer may be utilized to improve overall understanding the of the conditions under which measurements are taken. The accelerometer may be controlled by the processor of the processing module 410. In an example, a tri-axial accelerometer may be configured to indicate the activity and posture of the subject to improve the assessment of the signal conditions and reduce motion artifacts that could impact signal quality. If the subject is active, sedentary or supine, pooling or movement of fluid may normally occur which could potentially create false positives or negatives. An activity value may be generated based on the sensor data to determine an activity status of the user to reduce false positives.

The transceiver may communicate with a relay via Bluetooth, Bluetooth Low Energy, WiFi, or any other wireless transmission technology. The relay may be configured to receive analysis/results from the transceiver of the compression garment 400 and display the analysis/results on a user interface. In some embodiments, the relay may receive raw data from the transceiver of the compression garment 400 and transmit the raw data to a network device. The network device may be configured to determine a relative fluid content of the tissue based on the raw data associated with an energy level of the received signals. For example, should the fluid level increase, less energy will be reflected and the signal will decrease. Conversely, if less fluid is present, the signal level will increase. In this manner, the subcutaneous fluid detection system may measure and monitor the fluid content of a subject, for example to determine sub-clinical peripheral edema. The network device may be configured to transmit the analysis/results to the user interface for display or storage. The network device may be a cloud based system that is configured to receive, store, and process information to run predictive algorithms for review by caregivers (e.g., clinicians, etc.). The caregivers may send instructions to the compression garment 400 for further measurement information and alert the subject of actions that need to be taken. The user interface may include a cell phone, tablet/PC or discrete hub device that is connected to the internet via cellular modem, WiFi, direct cable, or any other communication link.

The power source of the processing module 410 may be an integrated rechargeable battery. Alternatively, the power source may be a primary battery.

The memory of the processing module 410 may include any computer-usable or computer-readable medium or device that can tangibly contain, store, communicate, or transport any signal or information that may be used by or in connection with any processor, for example processor 120 shown in FIG. 1. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof. Information derived from the one or more sensors 420A-420F, processor of the processing module 410, one or more detectors, or any combination thereof, may be stored in the memory of the processing module 410 until such time as it is available to be transmitted via the transceiver to the relay.

In some embodiments, the one or more sensors 420A-420F may each be configured for different measurements. For example, sensor 420A may be configured to measure temperature, sensor 420B may be configured to measure respiration, sensor 420C may be configured to measure pulse rate, and sensor 420D may be configured to measure fluid buildup.

The compression garment 400 may include any number of the sensors 420A-420F. In some embodiments, the compression garment may include only one sensor, whereas in other embodiments, the compression garment 400 may include multiple sensors. In some embodiments, the multiple sensors may include one or more sensors that are the same or one or more sensors that are different.

The compression garment 400 may be used to determine the effectiveness of the garment. For example, the compression garment 400 may be used to quantify the reduction level of fluid buildup in real-time to aid in the determination of when the garment may be removed from the subject. The example shown in FIG. 4 shows that the processing module 410 is separate from the one or more sensors 420A-420F, however, in some embodiments, the processing module 410 may be integrated into each of the one or more sensors 420A-420F. In some examples, the processing module 410, the one or more sensors 420A-420F, or any combination thereof, may be removable from the compression garment 400. For example, the compression garment 400 may include pockets to insert these components.

While the disclosure has been described in connection with certain embodiments, it is to be understood that the disclosure is not to be limited to the disclosed embodiments but, on the contrary, is intended to cover various combinations, modifications and equivalent arrangements included within the scope of the appended claims, which scope is to be accorded the broadest interpretation so as to encompass all such modifications and equivalent structures as is permitted under the law.

What is claimed is:

1. A compression garment for subcutaneous fluid detection, the compression garment comprising:
   a fabric that has a compression value of at least 5 mmHg;
   a processor embedded in the fabric;
   a sensor embedded in the fabric, wherein the sensor comprises:
   an emitter coupled to the processor, the emitter being configured to emit a signal into a subcutaneous tissue space of a subject, the signal being reflected by a subcutaneous tissue space; and
   a detector coupled to the processor, the detector being configured to determine an energy level based on the reflected signal;
   wherein the processor is configured to:
   measure a rate of change of a fluid buildup in the subcutaneous tissue space based on the energy level of the reflected signal; and
   determine a disease state of the subject based on the rate of change of the fluid buildup.

2. The compression garment of claim 1, wherein the emitter is configured to emit a light emitting diode (LED) wavelength.

3. The compression garment of claim 2, wherein the LED wavelength is configured to detect a pulse rate.

4. The compression garment of claim 2, wherein the emitter is further configured to emit a second LED wavelength, wherein the LED wavelength is 660 nm and the second LED wavelength is 940 nm to detect a peripheral capillary oxygen saturation (SPO2).

5. The compression garment of claim 2, wherein the LED wavelength is a near infrared (NIR) wavelength.

6. The compression garment of claim 5, wherein the NIR wavelength is 970 nm.

7. The compression garment of claim 1, further comprising:
   an accelerometer configured to detect activity of the subject to improve a signal condition.

8. The compression garment of claim 7, wherein the accelerometer is further configured to detect activity of the subject to reduce motion artifacts.

9. The compression garment of claim 1, further comprising:
   another sensor embedded in the fabric that is configured to determine a temperature of the subject.

10. A compression garment for subcutaneous fluid detection, the compression garment comprising:
    a fabric that has a compression value of at least 5 mmHg;
    a sensor embedded in the fabric, wherein the sensor comprises:
    a processor;
    an emitter coupled to the processor, the emitter being configured to emit a signal into a subcutaneous tissue space of a subject, the signal being reflected by a subcutaneous tissue space; and
    a detector coupled to the processor, the detector being configured to determine an energy level based on the reflected signal;
    wherein the processor is configured to:
    periodically determine a fluid buildup in the subcutaneous tissue space based on the energy level of the reflected signal;
    measure a rate of change of a fluid buildup in the subcutaneous tissue space based on the energy level of the reflected signal; and
    determine a disease state of the subject based on the rate of change of the fluid buildup.

11. The compression garment of claim 10, wherein the emitted signal is a light emitting diode (LED) wavelength.

12. The compression garment of claim 11, wherein the LED wavelength is configured to detect a pulse rate.

13. The compression garment of claim 11, wherein the emitter is further configured to emit a second LED wavelength, wherein the LED wavelength is 660 nm and the second LED wavelength is 940 nm to detect a peripheral capillary oxygen saturation (SPO2).

14. The compression garment of claim 11, wherein the LED wavelength is a near infrared (NIR) wavelength.

15. The compression garment of claim 14, wherein the NIR wavelength is 970 nm.

16. The compression garment of claim 10, further comprising detecting activity of the subject to improve a signal condition.

17. The compression garment of claim 16, wherein detecting activity of the subject is to reduce motion artifacts.

18. The compression garment of claim 10, further comprising displaying the determined fluid status.

* * * * *